US008129183B2

(12) United States Patent
Finocchiaro et al.

(10) Patent No.: US 8,129,183 B2
(45) Date of Patent: Mar. 6, 2012

(54) METHOD FOR STIMULATING DENDRITIC CELLS AND CELL PRODUCT THUS OBTAINED FOR THE AUTOLOGOUS IMMUNOTHERAPY OF SOLID HUMAN TUMOURS

(76) Inventors: Gaetano Finocchiaro, Milan (IT); Alfredo Martini, Milan (IT); Serena Pellegatta, Olginate (IT)

( * ) Notice: Subject to any disclaimer, the term of this patent is extended or adjusted under 35 U.S.C. 154(b) by 0 days.

(21) Appl. No.: 12/447,853

(22) PCT Filed: Oct. 30, 2007

(86) PCT No.: PCT/EP2007/009402
§ 371 (c)(1),
(2), (4) Date: Apr. 29, 2009

(87) PCT Pub. No.: WO2008/052740
PCT Pub. Date: May 8, 2008

(65) Prior Publication Data
US 2010/0071081 A1   Mar. 18, 2010

(30) Foreign Application Priority Data
Oct. 31, 2006   (IT) .............................. MI2006A2100

(51) Int. Cl.
*C12N 5/0784* (2010.01)
*C12N 5/095* (2010.01)
*A61K 39/00* (2006.01)

(52) U.S. Cl. ..... 435/325; 435/408; 424/93.7; 424/277.1
(58) Field of Classification Search .................. 435/325, 435/408; 424/277.1, 93.7
See application file for complete search history.

(56) References Cited

U.S. PATENT DOCUMENTS
2008/0206286 A1* 8/2008 Yu ............................ 424/277.1

FOREIGN PATENT DOCUMENTS
WO       02/12447 A2    2/2002
WO       2006/113181 A2  10/2006

OTHER PUBLICATIONS

Yu et al. (2004) Cancer Research, vol. 64, 4973-4979.*
Singh et al. (2003) Canc. Res., vol. 63, 5821-5828.*
Yamanaka et al. (2005) Clin. Canc. Res., vol. 11(11), 4160-4167.*
Banchereau, J. and Palucka, A. K., Dendritic Cells as Therapeutic Vaccines Against Cancer, www.nature.com/reviews/immunol, Apr. 2005, pp. 296-306, vol. 5, Nature Publishing Group.
Akasaki, Y., et al., Dendritic Cell-Based Immunotherapy for Malignant Gliomas, Expert Rev. Neurotherapeutics, 2005, pp. 497-508, 5, Future Drugs Ltd.
Pellegatta, S. and Finocchiaro, G., Cell Therapies in Neuro-Oncology, 2005, pp. S43-S52, 26, Neurol Sci.
Heimberger, A. B., et al., Bone Marrow-Derived Dendritic Cells Pulsed With Tumor Homogenate Induce Immunity Against Syngeneic Intracerebral Glioma, 2000, pp. 16-25, 103, Journal of Neuroimmunology.
Prins, R. M., et al., Immunotherapeutic Targeting of Shared Melanoma-Associated Antigens in a Murine Glioma Model, Dec. 1, 2003, pp. 8487-8491, 63, Cancer Research.
Kjaergaard, J., et al., Active Immunotherapy for Advanced Intracranial Murine Tumors by Using Dendritic Cell-Tumor Cell Fusion Vaccines, Jul. 2005, pp. 156-164, vol. 103, J. Neurosurg.
Kikuchi, T. et al., Vaccination of Glimoa Patients With Fusions of Dendritic and Glimoa Cells and Recombinant Human Interleukin 12, Nov./Dec. 2004, pp. 452-459, vol. 27, No. 6, J Immunother., Lippincott Williams & Wilkins.
Yu, J. S., et al., Vaccination With Tumor Lysate-Pulsed Dendritic Cells Elicits Antigen-Specific Cytotoxic T-Cells in Patients with Malignant Glioma, Jul. 15, 2004, pp. 4973-4979, 64, Cancer Research.
Yamanaka, R., et al., Clinical Evaluation of Dendritic Cell Vaccination for Patients With Recurrent Glioma: Results of a Clinical Phase I/II Trial, Jun. 1, 2005, pp. 4160-4167, 11, Clin Cancer Res.
Singh, S. K., et al., Identification of Human Brain Tumor Initiating Cells, Nov. 18, 2004, 396-401, vol. 432, Nature, Nature Publishing Group.
Galli, R., et al., Isolation and Characterization of Tumorigenic, Stem-Like Neural Precursors from Human Glioblastoma, Oct. 1, 2004, pp. 7011-7021, 64, Cancer Research.
Tunici, P., et al., Genetic Alterations and In Vivo Tumorigenicity of Neurospheres Derived from an Adult Glioblastoma, 2004, 3:25, Molecular Cancer, BioMed Central Ltd.
Kim, C. F., et al., Identification of Bronchioalveolar Stem Cells in Normal Lung and Lung Cancer, Jun. 17, 2005, pp. 823-835, vol. 121, Cell, Elsevier Inc.
Al-Hajj, M. et al., Prospective Identification of Tumorigenic Breast Cancer Cells, Apr. 1, 2003, pp. 3983-3988, vol. 100, No. 7, PNAS, USA.
Gibbs, C. P., et al., Stem-Like Cells in Bone Sarcomas: Implications for Tumorigenesis, Nov. 2005, pp. 967-976, vol. 7, No. 11, Neoplasia.
Fang, D., et al., A Tumorigenic Subpopulation with Stem Cell Properties in Melanomas, Oct. 15, 2005, 9328-9337, 65 (20), Cancer Research, American Association Cancer Research.
Mott, A., et al., Generation of Dendritic Cells from CD14+ Monocytes Positively Selected by Immunomagnetic Adsorption for Multiple Myeloma Patients Enrolled in a Clinical Trial of Anti-Idiotype Vaccination, 2003, pp. 240-250, 121, British Journal of Hematology, Blackwell Publishing Ltd. Mu, L.J., et al., A Protocol for Generation of Clinical Grade mRNA-Transfected Monocyte-Derived Dendritic Cells for Cancer Vaccines, 2003, pp. 578-586, 58, Scandinavian Journal of Immunology, Blackwell Publishing Ltd.
Ausman, J.I. et al., Studies on the Chemotherapy of Experimental Brain Tumors: Development of an Experimental Model, Sep. 1970, pp. 2394-2400, vol. 30, Cancer Research.
Herrlinger, U., et al., Vaccination for Experimental Gliomas Using GM-CSF-Transduced Glioma Cells, 1997, pp. 345-352, vol. 4, No. 6, Cancer Gene Therapy.
Plautz, G.E., et al., Treatment of Murine Gliomas by Adoptive Transfer of ex Vivo Activated Tumor-Draining Lymph Node Cells, 1997, pp. 101-107, 178, Cellular Immunology, Academic Press.

(Continued)

*Primary Examiner* — Anne Marie S Wehbe
(74) *Attorney, Agent, or Firm* — Amster, Rothstein & Ebenstein LLP

(57) ABSTRACT

In the ex vivo stimulation method of dendritic cells, the stimulation occurs with the lysate of tumor spheres (TS) of the solid tumors.

8 Claims, No Drawings

OTHER PUBLICATIONS

John S. Yu et al., Vaccination with Tumor Lysate-Pulsed Dendritic Cells Elicits Antigen-Specific, Cytotoxic T-Cells in Patients with Malignant Glioma, Cancer Res 2004.

Yuan Shao et al., Tissue-Specific Stem Cells—Nestin is Required for the Proper Self-Renewal of Neural Stem Cells, Stem Cells 2010:28:2162-2171; on-line at www.StemCells.com.

Florian T. Merkle et al., Radial glia give rise to adult neural stem cells in the subventricular zone, PNAS, Dec. 14, 2004; pp. 17528-17532, vol. 101, No. 5.

Takashi Shibata et al., Glutamate Transporter GLAST is Expressed in the Radial Glia-Astrocyte Lineage of Developing Mouse Spinal Cord, J. Neurosci., Dec. 1, 1997; 17(23):9212-9219.

Keith L. Ligon et al., Olig2-regulated lineage-restricted pathway controls replication competence in neural stem cells and malignant glioma, Neuron. Feb. 15, 2007, 53(4): 503-517.

Serena Pellegatta et al., Neurospheres Enriched in Cancer Stem-Like Cells are High Effective in Eliciting a Dendritic Cell-Medicated Immune Response . . . , Cancer Res 2006.

Ryuya Yamanaka et al., Clinical Evaluation of Dendritic Cell Vaccination for Patients with Recurrent Glioma: Results Clin. Phase I/II., Clin Cancer Res 2005:11(11) Jun. 1, 2005.

* cited by examiner

METHOD FOR STIMULATING DENDRITIC CELLS AND CELL PRODUCT THUS OBTAINED FOR THE AUTOLOGOUS IMMUNOTHERAPY OF SOLID HUMAN TUMOURS

The present invention refers to a method for the ex-vivo stimulation of dendritic cells and cell product thus obtained for the autologous immunotherapy of solid human tumours.

Vaccination with dendritic cells (DC) against cancer represents a therapeutic prospect of great interest (Bancherau, J. & Palucka, A. K. (2005) Nat Rev Immunol 5, 296-306).

Vaccination against gliomas in particular has attracted considerable attention, both at the pre-clinical and clinical level (Akasaki, Y., Black, K. L. & Yu, J. S. (2005) Expert Rev Neurother 5, 497-508; Pellegatta, S. & Finocchiaro, G. (2005) Neurol Sci 26 Suppl 1, S43-52).

Different murine models have shown the potential effectiveness of vaccination against the glioblastoma based on the inoculation of DC stimulated ex vivo with tumour extracts or peptides (Heimberger, A. B., Crotty, L. E., Archer, G. E., McLendon, R. E., Friedman, A., Dranoff, G., Bigner, D. D. & Sampson, J. H. (2000) J Neuroimmunol 103, 16-25; Prins, R. M., Odesa, S. K. & Liau, L. M. (2003) Cancer Res 63, 8487-91; Kjaergaard, J., Wang, L. X., Kuriyama, H., Shu, S. & Plautz, G. E. (2005) J Neurosurg 103, 156-64).

Moreover, the results of different clinical experiments have demonstrated that this therapeutic approach is not associated with significant toxicity (Kikuchi, T., Akasaki, Y., Abe, T., Fukuda, T., Saotome, H., Ryan, J. L., Kufe, D. W. & Olmo, T. (2004) J Immunother 27, 452-9; Yu, J. S., Liu, G., Ying, H., Yong, W. H, Black, K. L. & Wheeler, C. J. (2004) Cancer Res 64, 4973-9; Yamanaka, R., Homma, J., Yajima, N., Tsuchiya, N., Sano, M., Kobayashi, T., Yoshida, S., Abe, T., Narita, M., Takahashi, M. & Tanaka, R. (2005) Clin Cancer Res 11, 4160-7).

The identification of sub-populations of cells which are responsible for the tumorigenic nature of the GBM (cancer stem-like cells, CSC) could serve to strengthen the effects of the vaccination. CSC of GBM were identified by various groups: these cells can grow in standard conditions, i.e. adhering in the form of monolayers (GBM-AC) or as tumour spheres (GBM-TS). The CSC of GBM express stem cell markers and create gliomas similar to the original tumour when they are inoculated in SCID mice (Singh, S. K., Hawkins, C., Clarke, I. D., Squire, J. A., Bayani, J., Hide, T., Henkelman, R. M., Cusimano, M. D. & Dirks, P. B. (2004) Nature 432, 396; Galli, R., Binda, E., Orfanelli, U., Cipelletti, B., Gritti, A., De Vitis, S., Fiocco, R., Foroni, C., Dimeco, F. & Vescovi, A. (2004) Cancer Res 64, 7011-21; Tunici, P., Bissola, L., Lualdi, E., Pollo, B., Cajola, L., Broggi, G., Sozzi, G. & Finocchiaro, G. (2004) Mol Cancer 3, 25).

One object of the present invention is that of providing a method for ex vivo stimulation of human dendritic cells isolated from the human body, in order to use the cell product thus obtained for the autologous immunotherapy of solid human tumours.

These and other objects are attained with a method for ex vivo stimulation of human dendritic cells and a cell product in accordance with the claims.

Other characteristics of the invention are also described in the claims.

The invention is based on the surprising discovery that, in a murine model of gliobastoma, vaccination with dendritic cells stimulated with the lysate of gliobastoma stem cells cultivated in "tumour spheres" (TS) form ensures a significantly greater protection than that obtained by conducting the stimulation with a lysate of the same cells cultivated as adhesive cells in monolayer form. It is also based on the equally surprising discovery that in the mouse, the intracellular transplant of cells grown in NS form results more tumorigenic than the transplant of an equal number of cells grown in AC form.

In order to verify if the CSC can be a new target for the tumour therapy, and specifically for the immunotherapy with dendritic cells, we developed experiments aimed for dendritic cell targeting of CSCs derived from the glioma line GL261. In order to arrange CSC-enriched preparations, we cultivated cells derived from the tumour both in monolayer form (GBM-AC) and in tumour sphere form (GBM-TS). In particular, we obtained murine tumour spheres by making the GL261 cells grow in EGF and bFGF without serum. The GL261-TS had many important characteristics of TS from human GBM, and they surprisingly expressed marker levels of the radial glia which were higher than the cells GL261 which grew in standard conditions as monolayers (adhering GL261: GL261-AC), as verified by means of DNA microarray or PCR real-time.

The cerebral gliomas created by means of intracranial inoculation of cells coming from GL261-TC were more infiltrating and more quickly lethal than those caused by intracranial inoculations of an equal number of cells coming from GL261-AC, as shown by the survival analysis (p<0.0001), by the analysis with RM and by means of histology.

The dendritic cells (DC) were obtained from the bone marrow of syngeneic mice, used for the immunotherapy of tumours from GL261-TS and GL261-AC.

Unexpectedly, the immunotherapy carried out with the DC loaded with GL261-TS (DC-TC) resulted significantly more effective than that carried out with the same modes, but using DC loaded with GL261-AC (DC-AC). In particular, it was observed that the DC-TS were capable of curing 80% of the tumours from GL261-AC and 60% of the tumours from GL261-TS (p<0.0001), while the DC-AC were capable of curing only 50% of the tumours from GL261-AC (p<0.0022) and none of the tumours from GL261-TS. The GL261-TS expressed greater levels of MHCII and co-stimulatory molecules (CD80 and CD86) with respect to the GL261-AC.

The JAM assay indicated that splenocytes from GL261-TS had a greater lytic activity than the DC-AC splenocytes both on GL261-TS and on GL261-AC and immunohistochemical studies showed that vaccination with DC-TS is associated with a strong infiltration of the tumour by the lymphocytes CD8+ and CD4+.

These results suggest that the targeting by dendritic cells of CSC provides an effective level of protection against the GL261 gliomas, and that the protection provided by the immunotherapy conducted with DC loaded with tumour cells cultivated in TS form (DC-TS) resulted significantly more effective than the immunotherapy conducted with DC loaded with tumours cultivated in monolayer form (DC-AC).

The latter, unexpected result has potential implications for the design of clinical trials based on the vaccination with DC and for the immunotherapy of the solid human tumours.

A first application of our invention consists of the stimulation of human dendritic cells with TS derived from solid tumours.

The TS of solid tumours, such as (as non-limiting example), GBM, lung carcinomas, (Kim, C. F., Jackson, E. L., Woolfenden, A. E., Lawrence, S., Babar, I., Vogel, S., Crowley, D., Bronson, R. T. & Jacks, T. (2005) Cell 121, 823-35), breast carcinomas (Al-Hajj, M., Wicha, M. S., Benito-Hemandez, A., Morrison, S. J. & Clarke, M. F. (2003) Proc Natl Acad Sci USA 100, 3983-8), osteosarcoma (Gibbs, C. P., Kukekov, V. G., Reith, J. D., Tchigrinova, O., Suslov, O.

N., Scott, E. W., Ghivizzani, S. C., Ignatova, T. N. & Steindler, D. A. (2005) *Neoplasia* 7, 967-76) or melanoma (Fang, D., Nguyen, T. K., Leishear, K., Finko, R., Kulp, A. N., Hotz, S., Van Belle, P. A., Xu, X., Elder, D. E. & Herlyn, M. (2005) *Cancer Res* 65, 9328-37), are cultivated in TS form according to methods known by those skilled in the art.

The mononuclear cells from peripheral blood are obtained following leukapheresis from a patient in stationary conditions, using an apheresis unit (COBE Spectracell Separator).

After apheresis, the cells are incubated with clinical grade monoclonal antibody matched with magnetic microbeads (CliniMACS CD14 reagent, Miltenyi Biotec, Germany) and purified directly on CliniMACS.

The cells CD14+ are cultivated in CellGrow (CellGenix, Germany) grade clinical medium, in a "VueLife Teflon bag" sack (CellGenix, Germany), to a final concentration of $2\text{-}10\times 10^6$ cells/ml of medium in the presence of clinical grade GM-CSF and IL-4 (CellGenix, Germany), cytokines necessary for the differentiation from monocytes to immature dendritic cells. The culture sack is incubated at 37° C., 5% $CO_2$ for 5 days, without requiring any type of handling. After 5 days, before loading with the autologous tumour homogenate, the immature dendritic cells are incubated and loaded with the autologous tumour homogenate (using approximately 20-300 mg of homogenate per million cells), in the presence of 30-70 ug/ml of KLH (Keyhole Lympet Hemocianin, Calbiochem) as helper epitope for improving the immune response, for 24 hours. The subsequent maturation is induced by incubating the cells with pro-inflammatory cytokines (clinical grade, CellGenix, Germany), TNF-alpha, IL-1beta (10 ng/ml), IL-6, and prostaglandin $E_2$ ($PGE_2$; Pharmacia), for 24 hours. The dendritic cells thus stimulated at the end of the process are collected and frozen at a concentration of 1×10e7 cells/ml/vial and cryopreserved by using a freezing method with controlled temperature and speed, until immunotherapy use (Motta M R, Castellani S, Rizzi S, Curti A, Gubinelli F, Fogli M, Ferri E, Cellini C, Baccarani M, Lemoli R M (2003) *British Journal of Hematology* 121, 240-250; Mu L J, Gaudernack G., Saeboe-Larssen, Hammerstand H, Tierens A, Kvalheim G. (2003) *Scand Journ of Immunol* 58, 578-586).

A second application of our invention consists of a stimulation method of human dendritic cells with tumour stem cell-like cells (CSC) immunoseparated from TS obtained from solid tumours as described in the first application.

The immunoseparation of the CSC envisages a cell separation system based on the Milteny Biotec (Germany) MACS technology, which allows obtaining a magnetic enrichment of target cells expressing the antigen of interest and a depletion of undesired cells in a sterile system.

The system consists of a magnetic separation unit which includes a removable magnet and a support for the selection column constituted by a ferromagnetic matrix.

The cells are magnetically marked with an antibody chemically coupled to super-paramagnetic particles, which are made to pass over the column which retains the positive cells and allows the negative cells to flow past. After the removal of the column from the magnetic field, the cells are recovered and tested for the positivity of the chosen marker.

The selection of the cells to be separated is carried out based on the presence of the surface antigens, like CD133, but is not limited to the same. Recent studies indicate that such presence is associated with high tumorigenicity.

The dendritic cells of the tumour carrier are collected and prepared as is known to those skilled in the art and as reported in the first application.

A suspension of dendritic cells is incubated with a lysate of the CSCs according to methods known to those skilled in the art.

In our application, the preferred method envisages that the immature dendritic cells cultivated for 5 days (as described above) are incubated with the CSC homogenate (using approximately 100-700 mg of homogenate for million cells), in the presence of 30-70 ug/ml of KLH (Keyhole Lympet Hemocianin, Calbiochem) as helper epitope for improving the immune response, for 24 hours before maturation.

The dendrite cells thus stimulated at the end of the process are collected and frozen at a concentration of 1×10e7 cells/ml/vial and cryopreserved by using a freezing method with controlled temperature and speed until immunotherapy use.

A third application of our invention consists of a stimulation method of human dendritic cells with purified surface antigens from tumour stem cell-like cells (CSC) immunoseparated, as described in example 2, from TS obtained from solid tumours, as described in the first application.

The antigens of interest for the immunotherapy of tumours, such as CD133, are selected, separated and purified according to methods known by those skilled in the art.

One possible method provides for the isolation of peptides directly from the tumour. From the tumour fragments of patients, tumour cells are derived in culture. After a series of steps for their expansion, the cells are subjected to acidic elution, which provides for an incubation in the presence of a citrate-phosphate buffer (pH 3.2) in order to permit the dissociation of the peptides from the surface of the MHC-I.

A suspension of dendritic cells is incubated with a suspension/solution of the antigen peptides obtained as described above. In our application, the preferred method envisages that the immature dendritic cells are incubated for 24 hours before the maturation with pro-inflammatory cytokines, in the presence of the tumour-associated peptide solution at a concentration of 30-100 ug/ml.

The dendritic cells thus stimulated at the end of the process are collected and frozen at a concentration of 1×10e7 cells/ml/vial and cryopreserved using a freezing method with controlled temperature and speed, until immunotherapy use.

A fourth application of our invention provides that the stimulation of the dendritic cells is carried out by using single epitopes or a mixture of epitopes (natural or synthetic) derived from the surface antigens according to the third application. The natural peptides constitute the entire peptide repertory, both intracytoplasmatic and bonded to the MHCs of the tumour cells. They are therefore composed of a heterogeneous antigen mixture, hence favouring the possibility of activating a great number of precursors. Regarding the approach with the synthetic peptides, it is first of all necessary to synthesize a candidate tumour antigen, proceed with the prediction by means of an algorithm (TEPITOPE) of epitopes capable of binding different MHC alleles of class I in mixed manner, and subsequently verify the in vitro activation of lymphocytes T CD4+ with synthetic peptides corresponding to the predicted epitopes, and the recognition by the specific lymphocytes for the peptide of the native protein, in order to verify if the predicted epitope is a naturally processed epitope.

The epitopes are synthesized after identification of the chemical structure according to methods known by those skilled in the art. In particular, the synthesis of the epitopes can be carried out by means of automatic synthesisers and the purification by means of HPLC.

The preferred method provides that the immature dendritic cells are incubated for 24 hours before the maturation with pro-inflammatory cytokines in the presence of 10-100 ug/ml of the selected peptide.

A fifth application of our invention provides that the dendritic cells stimulated as described in the four applications reported above are used as a cell product for the autologous immunotherapy of solid human tumours, carried out according to methods known to those skilled in the art by intradermally and intratumourally administrating the dendritic cells themselves.

The above-described applications are reported as an example and are not in any manner limiting of the developments of our invention.

EXAMPLES

Example 1

Cultivation of the TS and AC

The GL261 tumour was originally induced through the intracranial injection of a chemical carcinogen, 3-3-methylcolanthrene, into C57BL6 mice and maintained through serial intracranial and subcutaneous transplants of small tumour fragments into the same murine strain (Ausman, 1970). The cell line was subsequently stabilised by a tumour fragment and was used as target of active immunotherapy strategies, adopted by numerous groups (Ausman J I, Shapiro W R, Rall D P (1970) *Cancer Res* 30, 2394-400; Herrlinger U, Kramm C M, Johnston K M, Louis D N, Finkelstein D, Reznikoff G, Dranoff G, Breakefield X O, Yu J S. (1997) *Cancer Gene Ther* 4, 345-52; Plautz G E, Touhalisky J E, Shu S. (1997) *Cell Immunol* 178, 101-7).

The GL261-AC grow in monolayers adhering to the plastic and were cultivated in our lab in DMEM medium enriched with 20% foetal bovine serum.

When cultivated in medium without serum and in the presence of EGF and bFGF, the GL261 lose the capacity to adhere in monolayers and grow as spheres in suspension, showing "self renewal" stem cell characteristics. The in vitro tests have shown that the GL261-TS proliferate less than the GL261-AC, but the kinetics of proliferation have shown that they proliferate at constant speed, while the GL261-AC cultivated in serum show an initial rapid proliferation followed by a plateau phase. GL261-TS cultivated with EGF/bFGF express nestin and other markers of radial glia. In differentiation conditions, without EGF/bFGF and in the presence of serum, they adhere to the plastic and express glial and neuronal markers.

Example 2

Stimulation of the Mouse Dendritic Cells

The dendritic cells derived from the bone marrow are selected from the entire hematopoietic stem cell population and in particular from the myeloid precursors, due to the presence of specific trophic factors in the culture medium.

For the differentiation and expansion of the dendritic cells, starting from the stem cell population obtained from the bone marrow, the complete enrichment of the medium is necessary with the granulocyte-macrophage growth factor (rmGM-CSF, recombinant murine granulocyte macrophage-colony stimulating factor) and with the interleukin 4 (rmIL-4) to 5 ng/ml concentration.

After seven days of differentiation, the immature dendritic cells are stimulated in vitro with an antigen "pool" deriving from GL261-TS cells or from GL261-AC cells and obtained by means of ultrasounding. The DC, both adhering and floating, are collected and resuspended at the concentration of $5-10\times10^6$ in 1 ml of the same medium and loaded with a lysate quantity equal to $50-600\,\mu g/10^6$ DC. In order to favour the phagocytosis of the extract by the dendritic cells, a cationic lipid reagent was used capable of forming liposomes which transport inside the cell nucleic acids, proteins and other antigen components deriving from the sonicated tumour cells.

The DC before and after the loading with the extract were characterised for the expression of surface markers specific for the dendritic population and specific for indicating the achieved maturation level.

Example 3

Immunotherapy with Dendritic Cells in GL261 Carrier Mice

The experimental scheme provides for three subcutaneous vaccinations of $1\times10^6$ DC, loaded and mature for every mouse: the first is carried out seven days after the intracranial inoculation of GL261-TS or GL261-AC, the second and third are spaced out by a week. The dendritic cells are differentiated and loaded with lysate of GL261-TS (DC-TS) or GL261-AC (DC-AC) with every treatment, no freezing of the DC is envisaged, neither immature nor mature DC.

The DC-TS were used against tumours from GL261-AC and GL261-TS and were shown to be effective in the remission of 80% ($p<0.0001$ survival time increase vs. controls) of the tumours from GL261-AC and 60% ($p<0.0001$ survival time increase vs. controls) of the tumours from GL261-TS. The DC-AC on the other hand showed a lower effectiveness, with remission of 50% of the tumours ($p<0.0022$ survival time increase vs. controls) from GL261-AC but none of the tumours from GL261-TS.

The effectiveness of the anti-tumour response was tested for each of the treatments, both in vitro by means of JAM assay, and in vivo with the characterisation of the lymphocyte infiltrates, and this has permitted confirming a more significant and massive response against the tumour, both from TS and from AC, when induced by DC-TS.

Example 4

Preparation and Stimulation of the Human Dendritic Cells

The dendritic cells are obtained starting from mononuclear cells of the peripheral blood by means of the use of a closed circuit system. The monocytes, characterised by the expression on the membrane surface of the marker CD14, are obtained starting from the leukapheresis product by using the CliniMacs instrument (Miltenij Biotec, Germany).

The cells CD14+ obtained by magnetic immunoseparation are cultivated for 5 days in CellGrow (CellGenix, Germany) clinical grade medium, in a "VueLife Teflon bag" sack (CellGenix, Germany), to a final concentration of 2-5×10e6 cells/ml of medium in the presence of clinical grade GM-CSF and IL-4 (CellGenix, Germany). The immature DC are incubated and loaded with 30-200 μg of TS homogenate obtained from the cultivation of the autologous tumour, in the presence of KLH (Keyhole Lympet Hemocianin) as helper epitope for improving the immune response, for 24 hours. The subsequent maturation is induced by incubating the cells with pro-inflammatory cytokines (clinical grade, CellGenix, Germany), TNF-alpha, IL-1beta, IL-6 (1000 U/ml) and prostaglandin $E_2$ ($PGE_2$), for 24 hours. The DC loaded and matured at the end of the process are frozen at a concentration of $1\times10e7$ cells/ml/vial and cryopreserved using a freezing method with controlled temperature and speed.

The invention claimed is:

1. A method of ex vivo stimulation of dendritic cells isolated from a human body, comprising stimulation of isolated human dendritic cells with lysate of tumor spheres (TS) of solid human tumors.

2. The method of ex vivo stimulation of dendritic cells according to claim 1, wherein the dendritic cells are stimulated in presence of adjuvants.

3. A cell product for the autologous immunotherapy of solid human tumors comprising the dendritic cells stimulated ex vivo according to the method of claim 1.

4. The cell product according to claim 3, wherein the solid tumor is a GMB or other cerebral tumor, a lung carcinoma or breast carcinoma, an osteosarcoma or a melanoma.

5. A formulation for autologous immunotherapy of solid human tumors comprising the cell product according to claim 3.

6. A formulation for the subcutaneous, intradermal, intramuscular, intrathecal or intratumoural administration for autologous immunotherapy of solid human tumors comprising a cell product having dendritic cells stimulated ex vivo according to the method of claim 1.

7. A cell product for autologous immunotherapy of solid human tumors, comprising the dendritic cells stimulated ex vivo according to the method of claim 2.

8. A formulation for autologous immunotherapy of solid human tumors comprising the cell product according to claim 4.

* * * * *